US00PP17644P2

(12) United States Plant Patent
Clifford et al.

(10) Patent No.: US PP17,644 P2
(45) Date of Patent: Apr. 24, 2007

(54) ***HOSTA* PLANT NAMED 'FOREST FIRE'**

(50) Latin Name: *Hosta hybrida*
Varietal Denomination: Forest Fire

(76) Inventors: John K. Clifford, Clifford's Perennial & Vine, Inc. P.O. Box 473, Paw Paw, MI (US) 49079; Ken J. Clifford, Clifford's Perennial & Vine, Inc. P.O. Box 473, Paw Paw, MI (US) 49079

( * ) Notice: Subject to any disclaimer, the term of this patent is extended or adjusted under 35 U.S.C. 154(b) by 0 days.

(21) Appl. No.: 11/250,101

(22) Filed: Oct. 13, 2005

(51) Int. Cl.
*A01H 5/00* (2006.01)

(52) U.S. Cl. ..... Plt./353
(58) Field of Classification Search ..... Plt./353
See application file for complete search history.

*Primary Examiner*—Kent Bell
(74) *Attorney, Agent, or Firm*—Penny J. Aguirre

(57) ABSTRACT

A new cultivar of *Hosta* named 'Forest Fire', a sport of *Hosta* 'Sagae', that is characterized by its variegated foliage having cordate-shaped leaves with glaucous green centers and margins that emerge yellow-green and turn creamy white as the leaf matures. A combination of new leaves and mature leaves results in a two-toned effect. The margins of 'Forest Fire' comprise about one fourth of the leaf area. 'Forest Fire' is a medium-large sized *Hosta* with an upright, mounded habit, and pale lavender flowers that are held above the foliage in mid summer.

2 Drawing Sheets

Botanical classification: *Hosta hybrida.*
Cultivar designation: 'Forest Fire'.

BACKGROUND OF THE INVENTION

The present invention, *Hosta* 'Forest Fire', relates to a new and distinct cultivar of *Hosta,* botanically known as a *Hosta hybrida,* hereinafter referred to as 'Forest Fire'.

The inventors discovered the new cultivar, 'Forest Fire', in 2000 in a cultivated growing area of a nursery in Tennessee. 'Forest Fire' originated as a naturally occurring whole plant mutation of *Hosta* 'Sagae' (unpatented).

Asexual reproduction of the new cultivar was first accomplished under the direction of the inventors utilizing *in vitro* propagation in The Netherlands in 2003. Asexual reproduction of the new cultivar by division and tissue culture has shown that the unique features of 'Forest Fire' are stable and reproduced true to type in successive generations.

SUMMARY OF THE INVENTION

The following traits have been repeatedly observed in trials in Michigan for a period of five years and represent the characteristics of the new cultivar. These attributes in combination distinguish 'Forest Fire' as a new and unique cultivar of *Hosta.*

1. The foliage of 'Forest Fire' is variegated with glaucous green centers and yellow-green margins that turn creamy white with maturity. The margins of 'Forest Fire' comprise about one fourth of the leaf area. New leaves of 'Forest Fire' emerge throughout the growing season with yellow-green margins combining with the mature foliage to give the overall plant a two-toned effect.
2. The leaves of 'Forest Fire' are cordate in shape with a variegation pattern in which the centers are feathered into the margin. An intermediate colored area exists that is also feathered into the margin.

3. 'Forest Fire' reaches a height of about 50 cm, exclusive of flower scapes, and a spread of about 50 cm in four years.
4. 'Forest Fire' blooms in mid summer with pale lavender flowers on scapes that arise above the foliage.

In comparison to the parent plant, 'Sagae', 'Forest Fire' has leaves with wider margins, leaves that are more cordate in shape, and the plant size of 'Forest Fire' is smaller in height and spread.

The closest comparison plant is *Hosta* 'Liberty' (U.S. Plant Pat. No. 12,531). In comparison, 'Forest Fire' has margins that are not as wide as 'Liberty' and the plant size of 'Forest Fire' is smaller in height and spread. The margins of 'Forest Fire' comprise about one fourth of the leaf whereas the margins of 'Liberty' comprise about one third of the leaf area.

BRIEF DESCRIPTION OF THE DRAWING

The accompanying colored photographs illustrate the overall appearance and distinct characteristics of the new *Hosta.* The photographs were taken in June of mature plants of 'Forest Fire' and 'Sagae' as grown outdoors in light shade for a period of five years.

Figure 1:
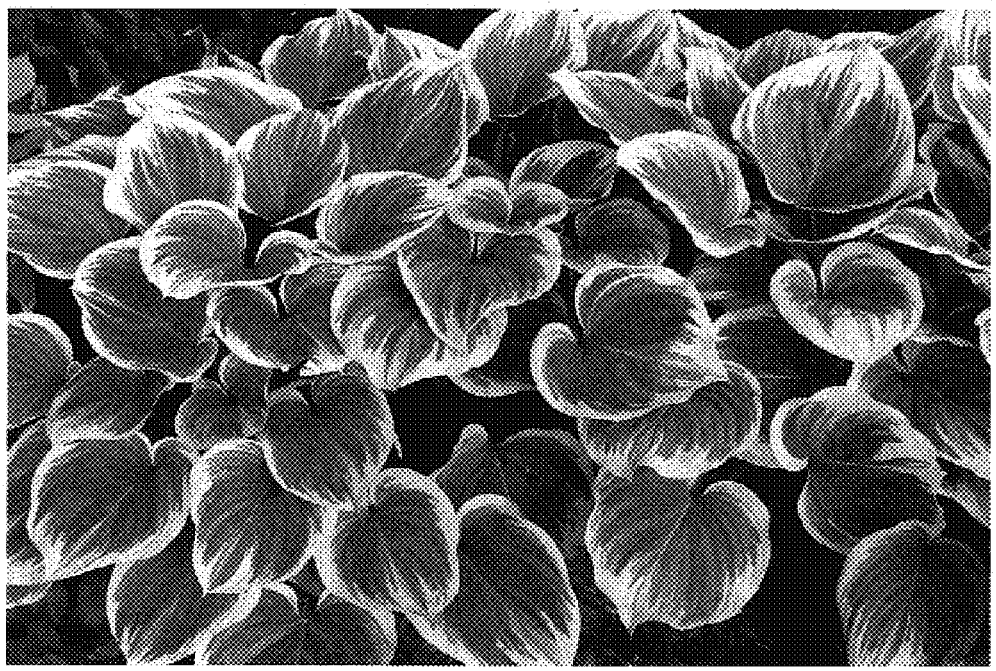
FIG. 1 provides an overall view of the foliage and plant habit of the new cultivar, 'Forest Fire'.
Figure 2:
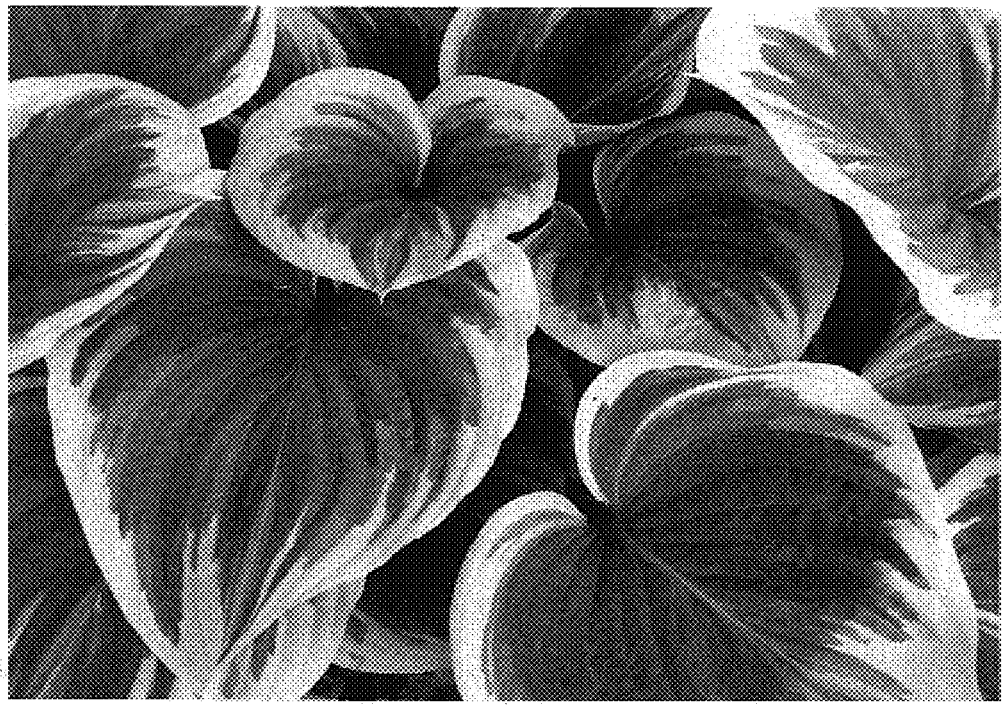
FIG. 2 provides a close-up view of the foliage of 'Forest Fire' and shows both newly emerged leaves and mature leaves.
Figure 3:
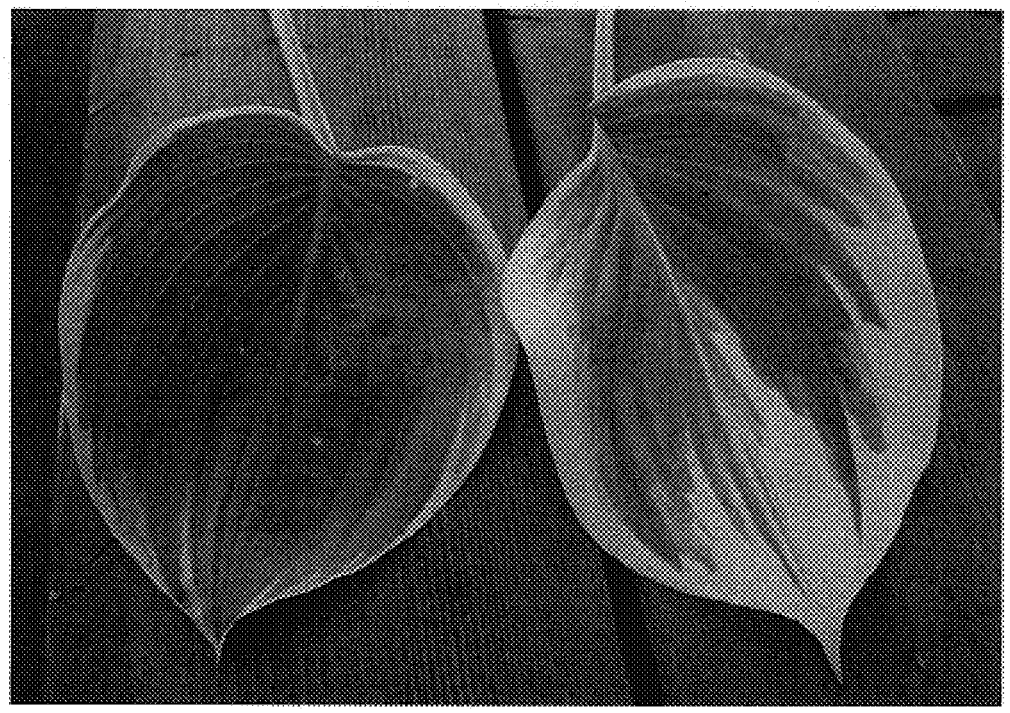
FIG. 3 provides a comparison between a leaf of 'Sagae' (shown on left) and 'Forest Fire' (shown on right).

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of five year-old plants of the new cultivar as grown outdoors in Paw Paw, Mich. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Forest Fire' is a cultivar of *Hosta hybrida*.

Parentage: Naturally occurring sport of *Hosta* 'Sagae' (not patented).

General description:

*Blooming period.*—About 3 weeks in mid summer in Michigan.

*Plant habit.*—Herbaceous perennial, clump-forming, upright and mounded foliage on a medium-large sized plant.

*Height and spread.*—Reaches about 50 cm in height (excluding flower scapes) and about 50 cm in width.

*Hardiness.*—USDA Zones 3–8.

*Culture.*—Light shade to medium shade, moist soils of moderate fertility.

*Diseases and pests.*—No susceptibility or resistance to diseases or pests has been observed for 'Forest Fire'.

*Root description.*—Freely branched, fleshy.

*Propagation.*—*In vitro* propagation is the preferred method utilizing typical methods for *Hosta,* division is also possible.

*Growth rate.*—Moderately vigorous.

Foliage description:

*Leaf shape.*—Broadly ovate when young, cordate when mature.

*Leaf division.*—Simple.

*Leaf base.*—Cordate.

*Leaf apex.*—Cuspidate.

*Leaf venation.*—About 11 pairs of veins, campylodrome pattern, impressed on upper surface and raised on lower surface, color matches leaf coloration.

*Leaf margins.*—Entire, gently undulated.

*Leaf attachment.*—Petiolate.

*Leaf arrangement.*—Basal, radiate spirally from base.

*Leaf surface.*—Upper slightly glaucous, lower glaucous.

*Leaf substance.*—Average to above average when mature.

*Leaf orientation.*—Held almost upright in relation to petioles.

*Leaf variegation pattern.*—Margins comprise about one fourth of the leaf area, ranging from about 0.5 to 2 cm on mature leaves, the centers are feathered into margins and an intermediate area exists between centers and margins, also in a feathered pattern. The new leaves emerging in summer with margins that are yellow-green, which combine with the mature leaves with creamy margins for a two-toned effect.

*Leaf color.*—Spring foliage, upper surface; centers 138A to 138B, margins 151B, intermediate area between the margins and centers 146C. Spring foliage, lower surface; centers 191A to 191B, margins 151C, intermediate area 191C. Mature summer foliage, upper surface; centers 137B, margins 8C to 8D, intermediate area 191C. Mature summer foliage, lower surface; centers 191A to 191B, margins 8C to 8D, intermediate area 191C and 144B. New summer foliage, upper surface; centers 137B, margins N144A to N144C, intermediate area 138B and 138C. New summer foliage, lower surface; centers 191B, margins 145A, intermediate area not distinct.

*Leaf size.*—Mature leaves average About 21 cm in length, about 21 cm in width.

*Leaf quantity.*—About 5 to 6 per shoot (eye).

*Petiole size.*—About 30 cm in length, about 1 cm in width.

*Petiole color.*—Mature leaves (inner and outer surface); 144A to 144B, narrow margins of N144D.

*Petiole surface.*—Slightly glaucous on inner surface, glabrous on outer surface.

*Petiole shape.*—Sulcate.

Flower scape description:

*Scape shape.*—Round, solid.

*Scape number.*—One per mature eye under normal growing conditions.

*Scape posture.*—Held upright to about 70° from horizontal.

*Scape size.*—About 80 cm in length, about 1 cm in width.

*Scape color.*—137B.

*Scape surface.*—Glaucous.

*Leaf bracts.*—About 3 per scape, centers are 137A in color, margins are 4B in color, ovate in shape, glaucous, average of 2 cm in length and 7 mm in width.

Flower description:

*Inflorescence type.*—Terminal racemes of funnel-shaped flowers on elongated scapes.

*Lastingness of inflorescence.*—About 3 weeks from first opening bloom to fading of last opening bloom, individual blooms last about one day.

*Flower shape.*—Funnel-shaped.

*Flower number.*—About 40 per scape.

*Flower fragrance.*—None.

*Flower bud shape.*—Spathulate.

*Flower bud size.*—Up to about 4 cm in length and 1.7 cm in diameter.

*Flower bud color.*—85C with markings of 85D.

*Flower size.*—About 5 cm in length and about 2.5 cm in diameter.

*Flower color.*—85D.

*Pedicels.*—About 1.5 cm in length, 2 mm in diameter, 91D in color.

*Perianth features.*—Comprised of 6 tepals, 3 interior and 3 exterior, overlapping in expanded region and fused in tube region.

*Tepal shape.*—Oblanceolate.

*Tepal size.*—About 5.5 cm in length, up to 1.5 cm in width.

*Tepal color.*—Outer and inner surface 85D with stripe of 155C on inner surface.

*Tepal texture.*—Glabrous.

*Floral bracts.*—1 per flower, ovate in shape, glaucous surface, 157C in color, about 1 cm in length and 8 mm in width.

Reproductive organs:

*Gynoecium.*—1 Pistil, about 6 cm in length, 155B in color, stigma is 3-lobed and 155B in color, ovary is superior, composed of 3 locules, 145C in color.

*Androecium.*—6 stamens, 8D in color, 5 to 6 cm in length, 1 mm in width, anthers are 3 mm in length, 1 mm in width, attachment is versatile, 202A in color, dehiscence is longitudinal, pollen is abundant and 8D in color.

*Fruit*.—Capsule, 3-chambered, about 6 cm in length, 6 mm in width, 137C in color.

*Seeds*.—About 35 seeds per capsule, about 3 mm in length and 1.5 mm in width, 200A in color.

We claim:

1. A new and distinct cultivar of *Hosta* plant named 'Forest Fire' as herein illustrated and described.

* * * * *